United States Patent [19]

Nakano et al.

[11] Patent Number: 5,250,260
[45] Date of Patent: Oct. 5, 1993

[54] TAPE FOR DETECTING HYDRIDES

[75] Inventors: Nobuo Nakano; Akihiro Yamamoto, both of Tokyo, Japan

[73] Assignee: Riken Keiki Co., Ltd., Tokyo, Japan

[21] Appl. No.: 969,447

[22] Filed: Oct. 30, 1992

[51] Int. Cl.⁵ ............................................. G01N 31/22
[52] U.S. Cl. ...................................... 422/56; 422/87; 436/73; 436/104; 436/169
[58] Field of Search .......................... 422/56–58, 422/87; 436/73, 104, 169

[56] References Cited

U.S. PATENT DOCUMENTS 4,420,567  12/1983  McMahon et al. ............... 436/73 X

*Primary Examiner*—Jill A. Johnston
*Attorney, Agent, or Firm*—Pollock, Vande Sande & Priddy

[57] ABSTRACT

A tape for detecting the presence of hydride gases by taking advantage of coloring reactions whose light sensitivity is lowered to a minimum without impairing the inherent mechanical strength of the reagent holder. The detection tape is prepared by impregnating a tape of porous cellulose fibers containing a gas adsorbent such as a powder of silica and a moisture keeper of glycerin with a coloring reagent of silver perchlorate or silver para-toluenesulfonate and a light resistance enhancer of para-toluenesulfonic acid. When the detection tape is exposed to a hydride gas contained in the sampled gas, silver perchlorate or silver para-toluenesulfonate is reduced by the hydride gas to form a colloid of silver that remains as a trace of reaction. As the amount of the colloid of silver is proportional to the concentration of the gas, the concentration of hydride gas can be determined by measuring the optical density of the trace of reaction. This tape does not discolor even after long storage as the light sensitivity of silver perchlorate and silver para-toluenesulfonate used as the coloring reagent is much lower than that of silver nitrate that has been used as the coloring reagent on the conventional detection tapes. Besides, the mechanical strength of the detection tape remains unimpaired because the acidity of para-toluenesulfonic acid added as the light resistance enhancer is not so strong as to damage the cellulose.

6 Claims, 5 Drawing Sheets

TAPE FOR DETECTING HYDRIDES

BACKGROUND OF THE INVENTION

1. Field of the Invention

This invention relates to a gas detection tape optimum for optically determining the concentration of a hydride gas from the trace of reaction between the hydride gas and a coloring reagent on a cellulose tape.

2. Description of the Prior Art

Being colorless, metallic hydrides, such as phosphine, silane, arsine and diborane, are very difficult to detect by the five senses of human beings. In the semiconductor industry where these highly toxic hydride gases are used, as such, provision of gas detectors to indicate their existence is compulsory. Common electrochemical or semiconductor gas sensors for other ordinary gases are unsuited because their sensitivity to hydride gases are extremely low. Usually, tapes that color when they come into contact and chemical reaction with hydride gases are used. The concentration of hydride gases is determined by measuring the optical density of the trace of their reaction.

Silver nitrate is a well-known reagent that colors when reacting with hydride gases. A hydride gas detection tape with silver nitrate comprises silver nitrate placed on a gas-permeable cellulose tape so that silver nitrate leaves a trace of the reaction of a colloid of silver on being exposed to and reduced by a hydride gas. The concentration of a hydride gas can be easily determined with high accuracy by measuring a change in the reflectance of the light thrown upon the trace of reaction formed on the tape.

However, silver nitrate is so sensitive to light that it is used as the coating emulsion on photographic films. As such, hydride gas detection tapes with silver nitrate must usually be kept in dark containers. Still, tapes once exposed to light become brown in about 24 hours even if they are kept in dark containers.

To eliminate this shortcoming, a detection tape with an improved light resistance was proposed (Japanese Provisional Patent Publication No. 99753 of 1983). The improved proved light resistance is obtained by reducing to a minimum the light-induced production of a colloid of silver by adding such strong acid as nitric acid to a cellulose tape impregnated with silver nitrate.

This type of hydride gas detection tapes prepared by the addition of silver nitrate remain intact enough to produce no error in measurement for about half a year when kept in dark containers.

However, nitric acid or other strong acid added for the improvement of light resistance attacks the cellulose holding the coloring reagent, thereby seriously impairing the mechanical strength of the detection tape over a long period of time.

The reduction of cellulose strength present a serious problem to the use in automatic measuring devices having a built-in gas sampler or optical gas concentration detec-tor. In this type of measuring device, the unused part of a hydride gas detection tape is exposed to the measuring area at given intervals to perform automatic measurement. For this reason, the detection tape set in the measuring device is passed over a storage reel and a take-up reel so that the tape can be taken up through the measuring area when required. At each measuring time, a given length of the unused part of the tape is paid off into the measuring area and, then, brought into contact with a sampled gas. Paid off under a considerable tension, the detection tape might break if it does not have adequate mechanical strength.

To provide a solution to this problem, the inventor proposed a hydride gas detection tape that has an improved light resistance without impairing the mechanical strength of the reagent holder. This hydride gas detection tape is prepared by using para-toluenesulfonic acid instead of nitric acid or other strong acids (Japanese Provisional Patent Publication No. 275352 of 1990). As no discoloration or nitration of cellulose occurs, the tape invariably remains the same as it was manufactured and thus permits a highly reliable automatic measurement of hydride gas.

SUMMARY OF THE INVENTION

However, the improved detection tape of the inventor has not been without problem. Moderate discoloration does occur when the tape is stored for a long time because light-sensitive silver nitrate is used as a coloring reagent. Even such moderate discoloration can lead to errors in the measurement of hydride gases with weak reducing powers.

To eliminate this shortcoming, a hydride gas detection tape according to this invention comprises a piece of porous cellulose containing a gas adsorbent and a moisture keeper and impregnated with silver perchlorate or silver para-toluenesulfonate as a coloring reagent and para-toluenesulfonic acid as a light resistance enhancer.

Silver perchlorate and silver para-toluenesulfonate used as the coloring reagent is much less sensitive to light than silver nitrate. On reacting with a hydride gas, however, they are reduced by the amount corresponding to the concentration of the hydride gas, precipitating a colloid of silver as a trace of the reaction. The concentration of the hydride gas can be determined by measuring the optical density of the trace of the reaction as the latter is proportional to the former.

The object of this invention is to provide a hydride gas detection tape that remains substantially immune to light without impairing the mechanical strength, particularly the tensile strength, of the coloring reagent holder.

DESCRIPTION OF THE PREFERRED EMBODIMENTS

First Preferred Embodiment

Cellulose tapes to hold a coloring reagent are prepared by shaping vegetable fibers into a gas-permeable sheet that is made as white as possible by bleaching. The sheet coated with a gas adsorbent, such as silicic acid, magnesium oxide or aluminum oxide, is then cut into tapes.

The gas adsorbent impregnated in the cellulose tape is intended to hold a gas, a liquid or a dissolved substance. The gas adsorbent, therefore, always keeps the moisture necessary for the reaction between a hydride gas and the coloring reagent and accelerates the reaction between the adsorbed hydride gas and silver perchlorate on the tape.

The cellulose tape thus prepared is impregnated with 0.5 to 4.0 grams of silver perchlorate, 0.3 to 3.0 grams of para-toluenesulfonic acid and about 25 grams of glycerin, each per square meter.

To be more specific, the cellulose tape is dipped in a solution prepared by dissolving 0.75 to 6.0 w/v percent of silver perchlorate, 0.5 to 4.5 w/v percent of para-toluenesulfonic acid and 15 v percent of glycerin in an organic solvent such as methanol to cause the tape to become impregnated with the solvent and dissolved substances. After pulling out the impregnated tape, the organic solvent is allowed to evaporate at room temperature, thereby causing silver perchlorate, para-toluenesulfonic acid and glycerin to remain on the tape. By implementing this process once or several times, depending on the concentration of the reagents contained in the solution, the tape is allowed to hold the desired amount of silver perchlorate per unit area thereof.

Figure 1:
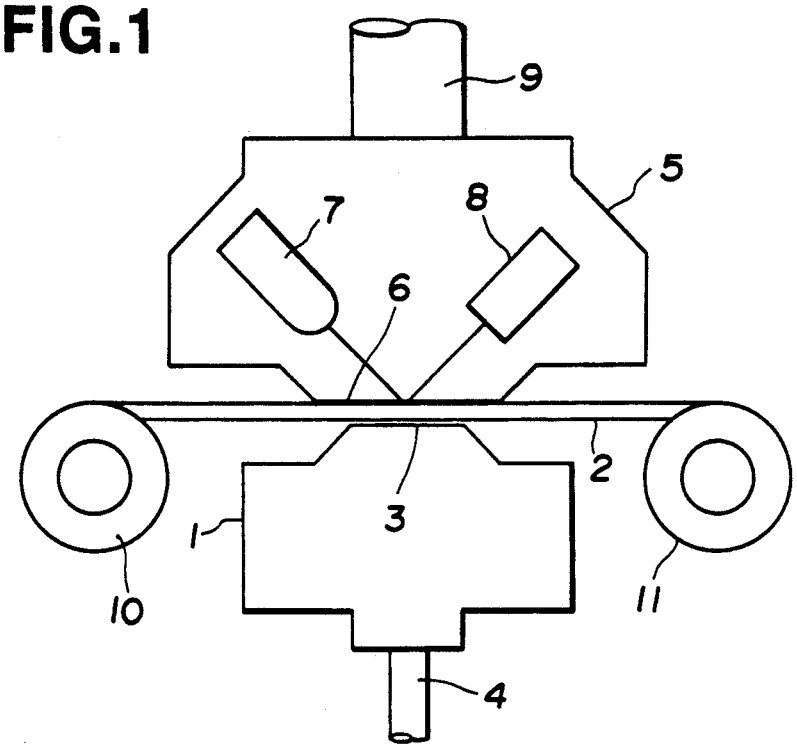
FIG. 1 shows the principle of a gas detector using a hydride gas detection tape according to this invention.

FIG. 1 shows an example of a device to determine the concentration of a gas with a gas detection tape. Reference numeral 1 designates a gas suction unit disposed to face the pathway of a tape 2, with a hole 3 with a diameter of approximately 1 cm perforated in the surface thereof facing the tape 2 so that a negative pressure, which is supplied from a suction pump not shown through a pipe 4, works thereon.

Reference numeral 5 denotes a measuring head disposed on that side of the tape 2 which faces the through hole 3 in the gas suction unit 1. The measuring head 5 is a light-shielded container having a hole positioned opposite to the hole in the suction unit 1. The measuring head 5 contains a light emitting element 7 and a light receiving element 8 disposed in such a positional relationship as to permit the detection of a trace of reaction formed on the tape 2, with a port 9 to introduce a gas to be detected being provided at one end thereof.

When the gas detection tape passed over reels 10 and 11 is set in position and a negative pressure drawn from the pump not shown is supplied into the suction unit 1, the gas to be detected flows from the intake port 9 to the measuring head 5. The gas flows further to the hole 6, passes over the detection tape 2, and flows outside through the hole 3. When the gas passes over the detection tape 2, silver perchlorate dissolved in glycerin and carried by the tape 2 selectively reacts with a hydride, such as phosphine, thereby precipitating a certain amount of a colloid of silver on the tape that is proportional to the concentration of phosphine.

When a given sampling time, such as approximately 20 seconds, is over, the suction of gas is stopped to proceed to the measurement of the optical density of the trace of reaction. The amount by which the light from the light emitting element 7 is absorbed depends on the optical density of the trace of reaction formed on the surface of the tape. Therefore, the concentration or the cumulative amount of a hydride passing through the tape can be determined by determining the optical density of the trace prior to the start of measurement or the difference in the optical density between the trace of measurement and the background of the tape. When the measurement of a sample is complete, the take-up reel 10 is driven to send an unused part of the tape is sent into the measuring area from the pay-off reel 11.

Figure 2:
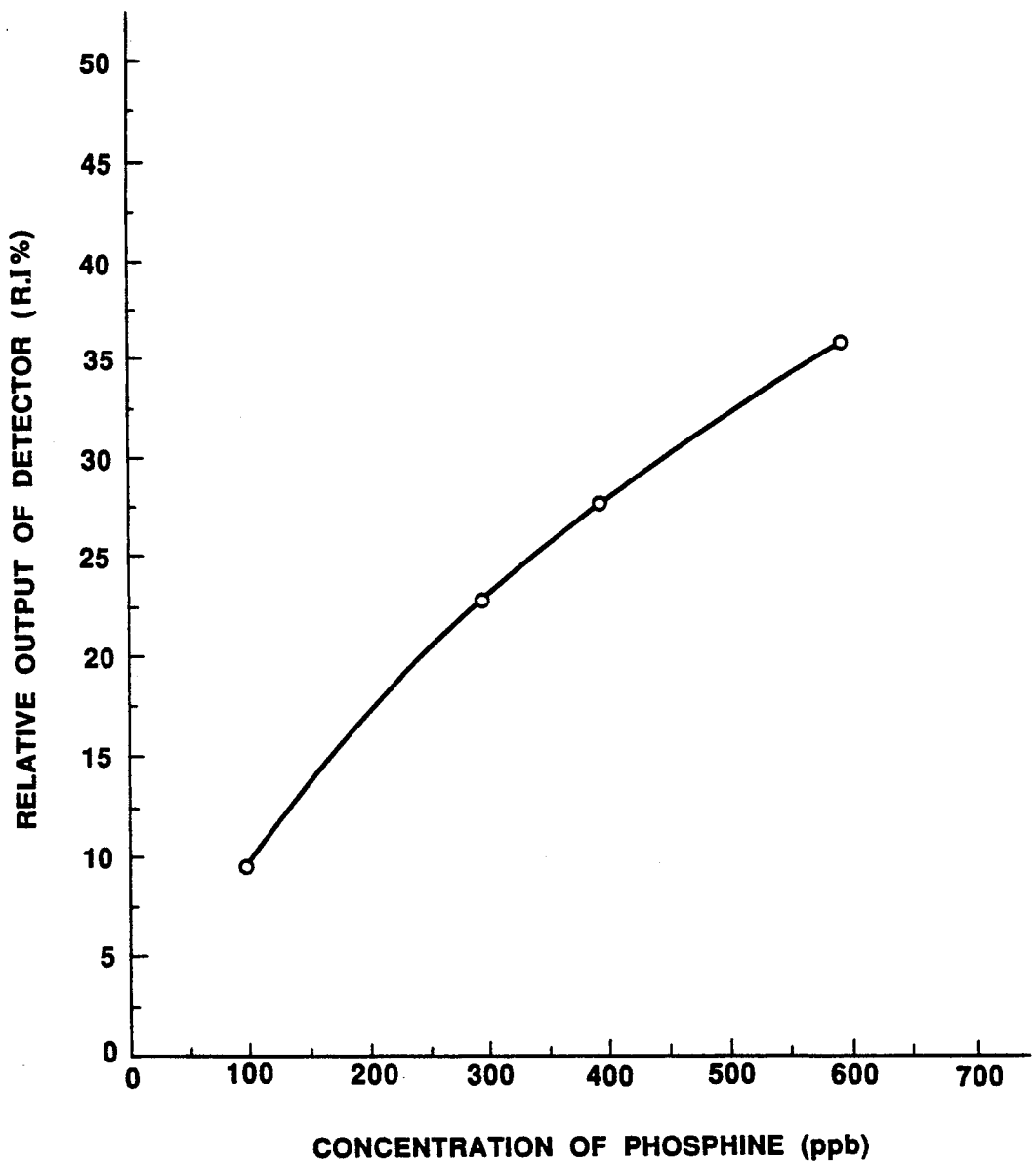
FIG. 2 shows a calibration curve of the sensitivity of a hydride gas detection tape according to this invention to phosphine.
Figure 4:
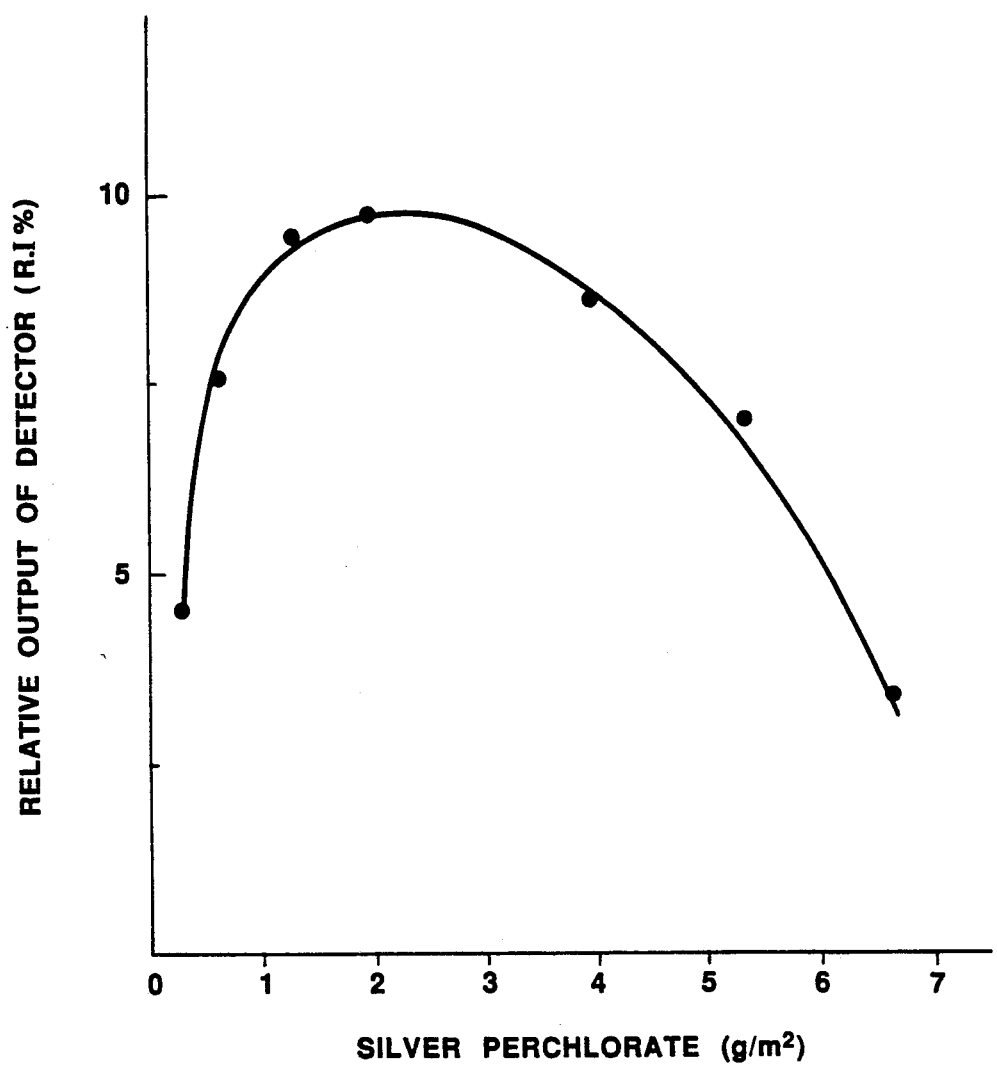
FIG. 4 diagrammatically shows the relationship between the concentration of silver perchlorate and the detection sensitivity of hydride gas.

FIG. 2 shows a calibration curve that indicates the output of the gas detector with a hydride gas detection tape according to this invention that was examined by changing the concentration of phosphine used as a typical example of hydride gases. As can be seen, there was a linear relationship between the output of the gas detector and the concentration of the hydride gas.

Besides, the sensitivity of the tape to the gas was in no way inferior to that of a newly made hydride gas detection tape that uses silver nitrate as the coloring reagent.

Figure 3:
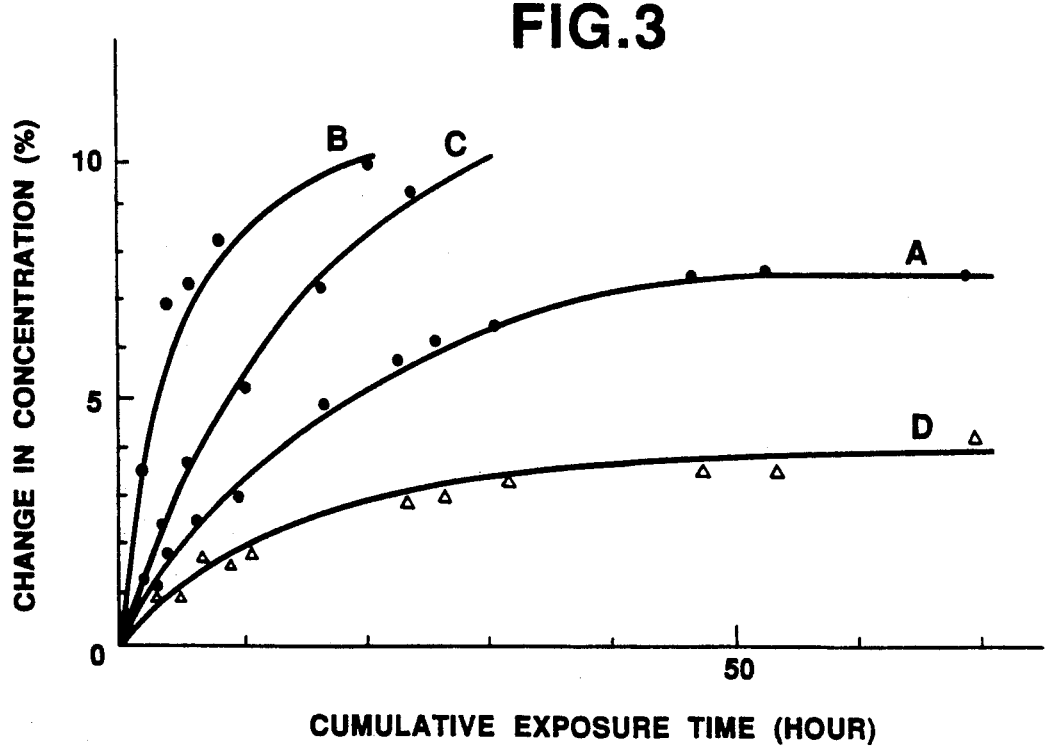
FIG. 3 diagrammatically shows the relationship between the exposure time and concentration change for hydride gas detection tapes according to this invention and the prior art.

FIG. 3 shows a change in the optical density of the same gas detection tape placed 20 cm directly below a 20 watt fluorescent lamp and exposed to a light (with an illumination intensity of approximately 1,500 lx) close to the natural one. The optical density of the unexposed hydride detection tape is used as the reference value $D_o$, whereas the optical density of the same tape after a given time is expressed as $D_t$. FIG. 3 shows the ratio of the difference between $D_t$ and $D_o$ to the reference density $D_o$.

As is obvious from FIG. 3, the ratio of the optical density change, ranging from $\frac{1}{3}$ to $\frac{1}{2}$, of the hydride gas detection tape according to this invention (indicated by a curve A) in relation to the exposure time is much smaller than that of a conventional tape with a coloring reagent of silver nitrate and a light resistance enhancer of nitric acid (indicated by curve B) and a tape with an increased mechanical strength attained by the use of para-toluenesulfonic acid in place of nitric acid (indicated by curve C), particularly in an early stage of exposure (with the cumulative exposure time not exceeding approximately 10 hours).

Under normal storage conditions, hydride gas detection tapes are hardly exposed to as much light as is comparable to the one in about 10 hours in the test described above. As such, the optical density of the hydride gas detection tapes according to this invention undergoes practically no change so long as they are stored in normal condition. As, in addition, the acidity of para-toluenesulfonic acid added as a light resistance enhancer is so low that the mechanical strength of cellulose used as the reagent holder remains unimpaired. Therefore, even a tape stored for a long time does not break when set for use on the gas detector.

The high light resistance of the hydride gas detection tapes of this invention permits high-precision measurement, particularly when the concentration of hydride gas contained in the sample is low or in the measurement of silane that does not react actively with the coloring reagent.

When tested on a paper tester of Instron Corp., the tensile strength of a hydride gas detection tape according to this invention was 0.55 kg/mm$^2$. By comparison, the tensile strength of a conventional tape that uses nitric acid as the light resistance enhancer was 0.4 kg/mm² or approximately 70 % that of the tape of this invention. This means that the hydride gas detection tapes according to this invention assure highly reliable automatic mea-surement on automatic hydride gas detectors.

Example

Cellulose tapes coated with a gas adsorbent were dipped in solutions prepared by dissolving 0.75 to 4.0 w/v percent of silver perchlorate, 0.5 to 4.5 w/v percent of para-toluenesulfonic acid and 15.0 w/v percent of glycerin in methanol. Then, methanol contained in the tapes pulled out of the solutions were allowed to evaporate at room temperature.

The tapes thus prepared carried 0.5 to 4.0 grams of silver perchlorate, 0.3 to 3.0 grams of para-toluenesulfonic acid and 25 grams of glycerin, each per square meter.

The influence of the concentration of silver perchlorate on detection sensitivity was studied. Practical detection sensitivity proved to be obtainable when the concentration of silver perchlorate is not lower than 0.5 gram per square meter. When the concentration exceeds 4 grams per square meter, detection sensitivity drops though the detection of gas is not impossible. Besides, the consumption of the coloring reagent increases to an economically disadvantageous extent.

Second Preferred Embodiment

Cellulose tapes to hold a coloring reagent are prepared by shaping vegetable fibers into a gas-permeable sheet that is made as white as possible by bleaching. The sheet coated with a gas adsorbent, such as silicic acid, magnesium oxide or aluminum oxide, is then cut into tapes.

The cellulose tape thus prepared is impregnated with not less than 0.3 gram of silver para-toluenesulfonate, 0.3 to 3.0 grams of para-toluenesulfonic acid and about 25 grams of glycerin, each per square meter.

To be more specific, the cellulose tape is dipped in a solution prepared by dissolving 0.5 to 2.0 w/v percent of silver para-toluenesulfonate, 0.5 to 4.5 w/v percent of para-toluenesulfonic acid and 15 v percent of glycerin in an organic solvent such as methanol to cause the tape to become impregnated with the solvent and dissolved substances. After pulling out the impregnated tape, the organic solvent is allowed to evaporate at room temperature, thereby causing silver para-toluenesulfonate, para-toluenesulfonic acid and glycerin to remain on the tape. By implementing this process once or several times, depending on the concentration of the reagents contained in the solution, the tape is allowed to hold the desired amount of silver perchlorate per unit area thereof.

Figure 5:
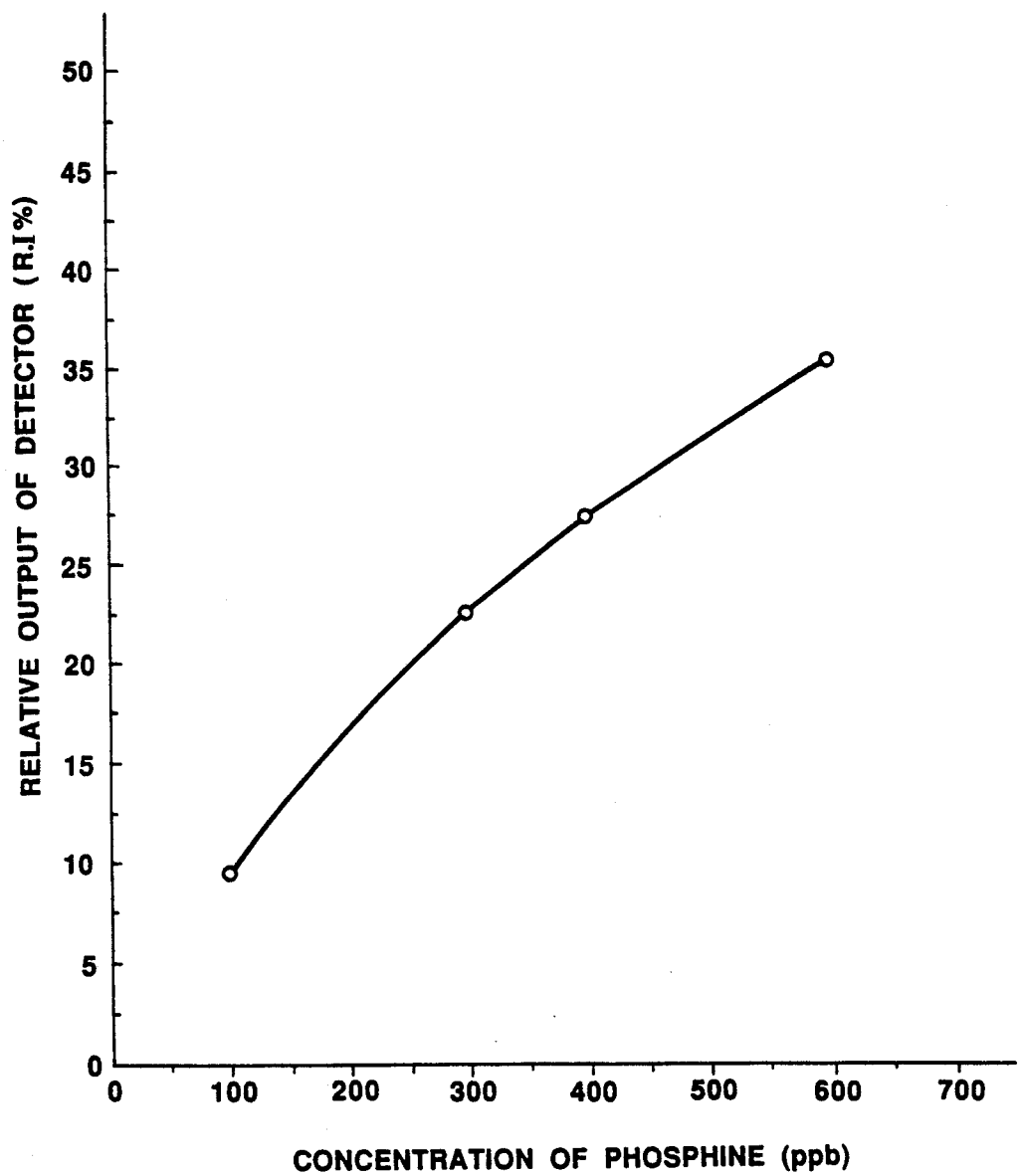
FIG. 5 shows a calibration curve of the sensitivity of a hydride gas detection tape according to this invention to phosphine.
Figure 6:
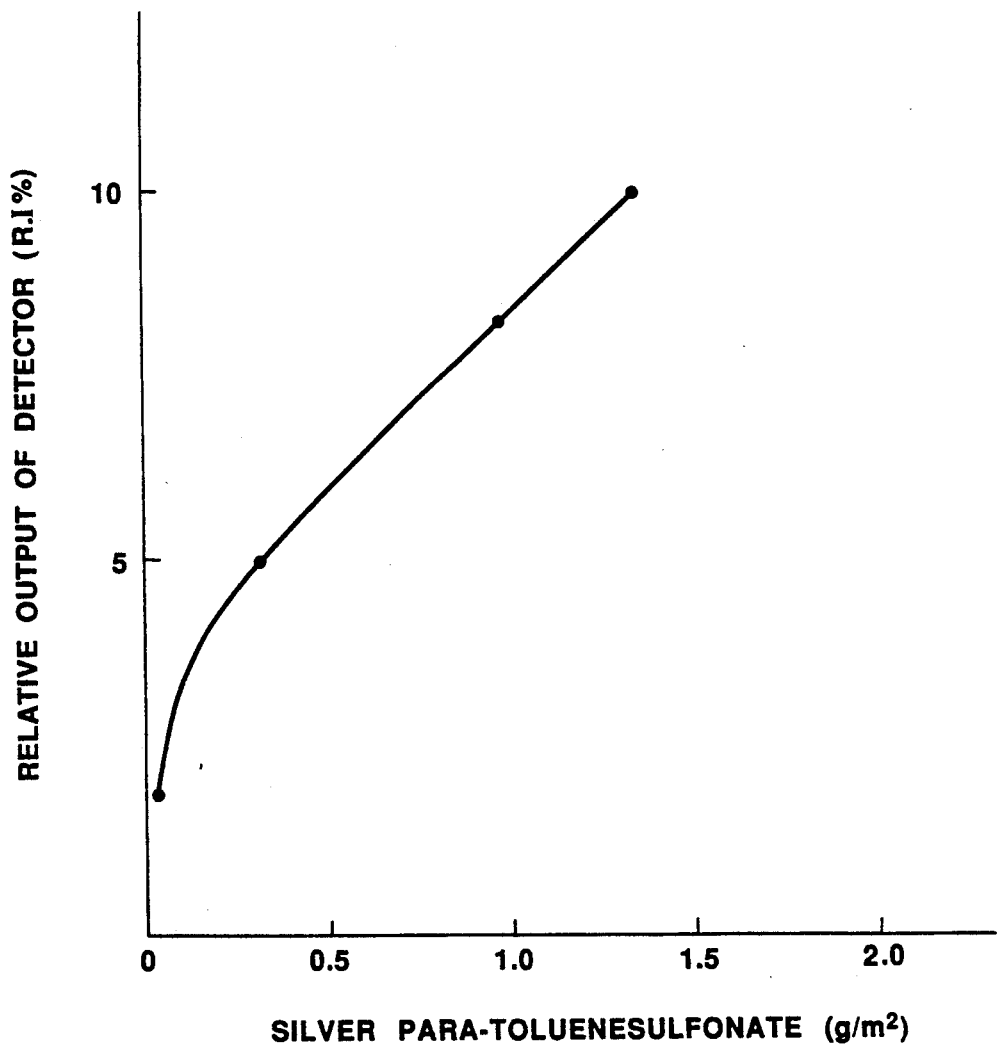
FIG. 6 diagrammatically shows the relationship between the concentration of silver para-toluenesulfonate and the sensitivity of a hydride gas detection tape.

FIG. 5 shows a calibration curve that indicates the output of the gas detector with a hydride gas detection tape according to this invention that was examined by changing the concentration of phosphine used as a typical example of hydride gases. As can be seen, there was a linear relationship between the output of the gas detector and the concentration of the hydride gas.

Besides, the sensitivity of the tape to the gas was in no way inferior to that of a conventional hydride gas detection tape that uses silver nitrate as the coloring reagent.

A change in the optical density of the same gas detection tape placed 20 cm directly below a 20 watt fluorescent lamp and exposed to a light (with an illumination intensity of approximately 1,500 lx) close to the natural one was studied. The ratio of the optical density change, ranging from ¼ to ⅓ of the hydride gas detection tape according to this invention (indicated by a curve D) in relation to the exposure time is much smaller than that of a conventional tape with a coloring reagent of silver nitrate and a light resistance enhancer of nitric acid (indicated by curve B) and a tape with an increased mechanical strength attained by the use of para-toluenesulfonic acid in place of nitric acid (indicated by curve C), particularly in an early stage of exposure (with the cumulative exposure time not exceeding approximately 10 hours). The ratio was also smaller than that of the first preferred embodiment of this invention described before (indicated by a curve A).

Under normal storage conditions, hydride gas detection tapes are hardly exposed to as much light as is comparable to the one in about 10 hours in the test described above. As such, the optical density of the hydride gas detection tapes according to this invention undergoes practically no change so long as they are stored in normal condition. Actually, no marked discoloration occurred on the tape allowed to stand in a room.

The high light resistance of the hydride gas detection tapes of this invention permits measuring the concentration of a hydride gas that is lower than that can be determined by the first preferred embodiment of this invention or the concentration of silane that does not react actively with the coloring reagent with still higher accuracy.

Example

Cellulose tapes coated with a gas adsorbent were dipped in solutions prepared by dissolving not less than 0.5 w/v percent of silver para-toluenesulfonate (the solution becomes saturated with approximately 4 w/v percent of silver para-toluenesulfonate at the most at room temperature as the solubility thereof is very low), 0.5 to 4.5 w/v percent of para-toluenesulfonic acid and 15 0 w/v percent of glycerin in methanol. Then, methanol contained in the tapes pulled out of the solutions were allowed to evaporate at room temperature.

The tapes thus prepared carried 0.3 to 1.4 grams of silver para-toluenesulfonate, 0.3 to 3.0 grams of para-toluenesulfonic acid and 25 grams of glycerin, each per square meter.

The influence of the concentration of silver para-toluenesulfonate on detection sensitivity was studied. Practical detection sensitivity proved to be obtainable when the concentration of silver para-toluenesulfonate is not lower than 0.3 gram per square meter. Not more than approximately 1.4 grams per square meter of silver para-toluenesulfonate can be coated at a time because of the extremely low solubility thereof. When the concentration of silver para-toluenesulfonate exceeds this limit, the consumption of the coloring reagent increases to an economically disadvantageous extent.

In the description of the first and second preferred embodiments, phosphine was cited as an example of hydride gases. It has been confirmed that the detection tapes according to this invention also exhibit similar sensitivity in the detection of such other hydride gases as arsine, diborane, silane, disilane, hydrogen selenide, germane and hydrogen sulfide that show common chemical reactions with coloring reagents.

As described above, a hydride gas detection tape according to this invention are prepared by impregnating a porous tape-shaped holder containing a gas adsorbent and a moisture keeper with a coloring reagent of silver perchlorate or silver para-toluenesulfonate and a light resistance enhancer of para-toluenesulfonic acid. The hydride gas detection tape thus prepared not only exhibits an extremely high light resistance but also maintains adequate tensile strength as no strong acid is used in the preparation thereof.

What is claimed is:

1. A hydride gas detection tape which comprises a piece of gas-permeable cellulose containing a gas adsorbent and a moisture keeper impregnated with a coloring reagent of silver perchlorate and a light resistance enhancer of para-toluenesulfonic acid, whereby hydride gas reacts with said coloring reagent to produce a color change indicative of the presence of hydride gas.

2. A hydride gas detection tape according to claim 1, in which the piece of gas-permeable cellulose is impregnated with 0.5 to 4.0 grams per square meter of silver perchlorate.

3. A hydride gas detection tape according to claim 1 or 2, in which the piece of gas-permeable cellulose is impregnated with 0.3 to 3.0 grams per square meter of para-toluenesulfonic acid.

4. A hydride gas detection tape which comprises a piece of gas-permeable cellulose containing a gas adsorbent and a moisture keeper impregnated with a coloring reagent of silver para-toluenesulfonate and a light resistance enhancer of para-toluenesulfonic acid, whereby hydride gas reacts with said coloring reagent to produce a color change indicative of the presence of hydride gas.

5. A hydride gas detection tape according to claim 4, in which the piece of gas-permeable cellulose is impregnated with at least 0.3 gram per square meter of silver para-toluenesulfonate.

6. A hydride gas detection tape according to claim 4 or 5, in which the piece of gas-permeable cellulose is impregnated with 0.3 to 3.0 grams per square meter of para-toluenesulfonic acid.

* * * * *

UNITED STATES PATENT AND TRADEMARK OFFICE
CERTIFICATE OF CORRECTION

PATENT NO. : 5,250,260

DATED : October 5, 1993

INVENTOR(S) : Nakano et al

It is certified that error appears in the above-identified patent and that said Letters Patent is hereby corrected as shown below:

On the title page, please inser the following:

--[30]   Foreign Application Priority Data

Jul. 2, 1992   [JP]   Japan ...........199222
    Jul. 2, 1992   [JP]   Japan ...........199223

Signed and Sealed this

Seventeenth Day of May, 1994

Attest:

BRUCE LEHMAN

Attesting Officer     Commissioner of Patents and Trademarks